United States Patent
Compton et al.

(10) Patent No.: US 8,860,933 B2
(45) Date of Patent: Oct. 14, 2014

(54) MULTI-AXIS ATOMIC INERTIAL SENSOR SYSTEM

(71) Applicant: Honeywell International Inc., Morristown, NJ (US)

(72) Inventors: Robert Compton, Plymouth, MN (US); Benjamin Mohr, St. Louis Park, MN (US); Nicholas C. Cirillo, Jr., Bloomington, MN (US)

(73) Assignee: Honeywell International Inc., Morristown, NJ (US)

( * ) Notice: Subject to any disclaimer, the term of this patent is extended or adjusted under 35 U.S.C. 154(b) by 235 days.

(21) Appl. No.: 13/661,809

(22) Filed: Oct. 26, 2012

(65) Prior Publication Data

US 2014/0016118 A1 Jan. 16, 2014

Related U.S. Application Data

(60) Provisional application No. 61/670,797, filed on Jul. 12, 2012.

(51) Int. Cl.
*G01N 21/00* (2006.01)
*G01N 21/64* (2006.01)

(52) U.S. Cl.
CPC ............. *G01N 21/64* (2013.01); *G01N 21/00* (2013.01)
USPC ............. 356/72; 356/460; 73/1.37; 73/1.38; 73/504.01; 702/104; 702/141; 702/96

(58) Field of Classification Search
CPC ... G01N 21/64; G01N 21/00; G01N 21/3504; G01N 21/47; G01N 21/55; G01C 19/58; G01C 21/16; G01P 15/08; G01P 21/00; G01B 11/14

USPC ........ 356/72, 460; 73/1.37, 504; 702/104, 96, 702/141

See application file for complete search history.

(56) References Cited

U.S. PATENT DOCUMENTS

| | | | |
|---|---|---|---|
| 3,761,721 A | 9/1973 | Altshuler et al. | |
| 4,992,656 A | 2/1991 | Clauser | |

(Continued)

FOREIGN PATENT DOCUMENTS

| | | |
|---|---|---|
| EP | 0511119 | 5/1995 |
| EP | 2629303 | 8/2013 |
| WO | 2007002327 | 1/2007 |

OTHER PUBLICATIONS

European Patent Office, European Search Report, from Foreign Counterpart of U.S. Appl. No. 13/758,370, Nov. 8, 2013, pp. 1-3, Published in: EP.

(Continued)

*Primary Examiner* — Tarifur Chowdhury
*Assistant Examiner* — Isiaka Akanbi
(74) *Attorney, Agent, or Firm* — Fogg & Powers LLC

(57) ABSTRACT

An inertial sensing system comprises a first multi-axis atomic inertial sensor, a second multi-axis atomic inertial sensor, and an optical multiplexer optically coupled to the first and second multi-axis atomic inertial sensors. The optical multiplexer is configured to sequentially direct light along different axes of the first and second multi-axis atomic inertial sensors. A plurality of micro-electrical-mechanical systems (MEMS) inertial sensors is in operative communication with the first and second multi-axis atomic inertial sensors. Output signals from the first and second multi-axis atomic inertial sensors aid in correcting errors produced by the MEMS inertial sensors by sequentially updating output signals from the MEMS inertial sensors.

20 Claims, 3 Drawing Sheets

(56) References Cited

U.S. PATENT DOCUMENTS

| | | | |
|---|---|---|---|
| 5,052,808 A | 10/1991 | Hilby et al. | |
| 5,274,231 A | 12/1993 | Chu et al. | |
| 6,456,939 B1 | 9/2002 | McCall et al. | |
| 6,606,908 B2 | 8/2003 | Johann et al. | |
| 6,647,352 B1 * | 11/2003 | Horton | 702/151 |
| 6,697,736 B2 * | 2/2004 | Lin | 701/472 |
| 7,728,587 B2 * | 6/2010 | Stewart et al. | 324/304 |
| 7,847,924 B2 * | 12/2010 | Aarons et al. | 356/28.5 |
| 7,995,630 B2 | 8/2011 | Rakuljic | |
| 8,459,093 B2 * | 6/2013 | Donadel et al. | 73/1.37 |
| 8,583,371 B1 * | 11/2013 | Goodzeit et al. | 701/501 |
| 2005/0125141 A1 * | 6/2005 | Bye | 701/200 |
| 2006/0249666 A1 * | 11/2006 | Kasevich et al. | 250/251 |
| 2010/0149025 A1 * | 6/2010 | Meyers et al. | 342/357.02 |
| 2010/0149541 A1 | 6/2010 | Aarons et al. | |
| 2014/0022534 A1 | 1/2014 | Strabley et al. | |

OTHER PUBLICATIONS

European Patent Office, Office Action from EP Application No. 13171764.7 mailed Dec. 17, 2013, from Foreign Counterpart of U.S. Appl. No. 13/758,370, Dec. 17, 2013, pp. 1-7, Published in: EP.

U.S. Patent and Trademark Office, Office Action, from U.S. Appl. No. 13/758,370, Mar. 21, 2014, pp. 1-55, Published in: US.

* cited by examiner

MULTI-AXIS ATOMIC INERTIAL SENSOR SYSTEM

This application claims the benefit of priority to U.S. Provisional Application No. 61/670,797, filed on Jul. 12, 2012, the disclosure of which is incorporated by reference.

BACKGROUND

Cold atom interferometers are the basis for a newer class of inertial sensors. Analogous to the function of a fiber optic or ring laser gyroscope, inertial forces induce phase shifts in the quantum mechanical wave function of atoms traversing a loop in a cold atom interferometer.

For some operating parameters, cold atom inertial sensors may provide a lower update rate than desirable. In such cases, micro-electrical-mechanical systems (MEMS) inertial sensors may be used as a sort of flywheel to provide continuous output between atomic sensor readings. In this situation, the atomic inertial sensor can be used to correct bias and scale factor drift in the MEMS inertial sensor.

In order to minimize size, weight, and power, it is desirable to make the atomic inertial sensor as small as possible. Unfortunately, sensitivity scales unfavorably with reduced sensor size. A minimum atomic inertial sensor volume of approximately 6 $cm^3$ is necessary to meet some performance metrics. However, the total volume metric for a six degree of freedom atomic inertial measurement unit (IMU) is required for some applications to be less than 20 $cm^3$.

SUMMARY

An inertial sensing system comprises a first multi-axis atomic inertial sensor, a second multi-axis atomic inertial sensor, and an optical multiplexer optically coupled to the first and second multi-axis atomic inertial sensors. The optical multiplexer is configured to sequentially direct light along different axes of the first and second multi-axis atomic inertial sensors. A plurality of MEMS inertial sensors is in operative communication with the first and second multi-axis atomic inertial sensors. Output signals from the first and second multi-axis atomic inertial sensors aid in correcting errors produced by the MEMS inertial sensors by sequentially updating output signals from the MEMS inertial sensors.

DRAWINGS

Understanding that the drawings depict only exemplary embodiments and are not therefore to be considered limiting in scope, the exemplary embodiments will be described with additional specificity and detail through the use of the accompanying drawings, in which.

DETAILED DESCRIPTION

Figure 1:
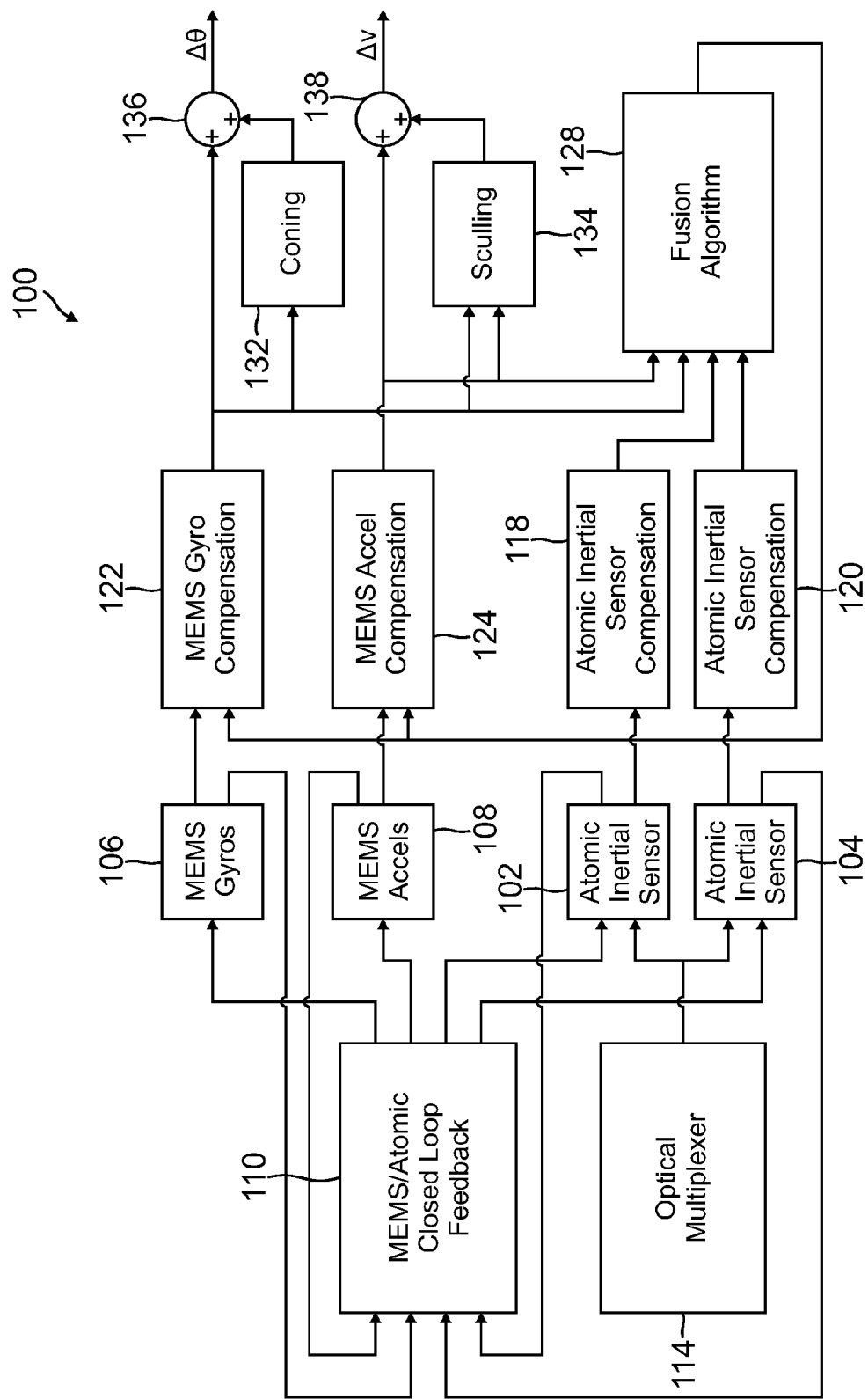
FIG. 1 is a block diagram of an inertial sensing system that employs multi-axis atomic inertial sensors according to one embodiment.

In the following detailed description, reference is made to the accompanying drawings that form a part hereof, and in which is shown by way of illustration specific illustrative embodiments. It is to be understood that other embodiments may be utilized and that logical, mechanical, and electrical changes may be made. The following detailed description is, therefore, not to be taken in a limiting sense.

Multi-axis atomic inertial sensors are provided that can be implemented in an inertial sensing system and method to aid in error correction of conventional inertial sensors. The multi-axis atomic inertial sensors are configured such that their sense axes can be repeatedly changed using switching optics to sequentially correct errors in the conventional inertial sensors.

In one embodiment, the multi-axis atomic inertial sensors can be implemented with a six degree of freedom inertial sensing system, such as an IMU, which measures acceleration and rotation in three axes. The outputs from the conventional inertial sensors in the IMU are disciplined to the atomic inertial sensors such that much of the bias and scale factor errors are removed from the conventional inertial sensors.

Although the use of MEMS inertial sensors is described in various embodiments as follows, other conventional inertial sensors can be fused with the multi-axis atomic inertial sensors in a similar fashion.

In one embodiment, an inertial sensing system comprises a pair of multi-axis atomic inertial sensors, and an optical multiplexer operatively coupled to the multi-axis atomic inertial sensors. The optical multiplexer includes a plurality of optical switches configured to sequentially direct light along different axes of the first and second multi-axis atomic inertial sensors. A plurality of MEMS inertial sensors, such as six MEMS inertial sensors (e.g., three MEMS gyroscopes and three MEMS accelerometers), is in operative communication with the multi-axis atomic inertial sensors. Output signals from the multi-axis atomic inertial sensors aid in correcting errors produced by the MEMS inertial sensors by sequentially updating the output signals of the MEMS inertial sensors.

In one example, cycle time for each atomic sensor is about 20 ms. Approximately 10 ms is required to prepare a sample of cold atoms, and approximately another 10 ms to interrogate the atoms to extract inertial information. It should be noted that these times are parameters that can be varied depending on performance tradeoffs, such as bandwidth versus sensitivity.

Acceleration and rotation are entangled in each measurement, so simultaneous measurements of reciprocal atomic sensors are required to separate acceleration from rotation. A minimum of two atomic sensor bodies are therefore needed. Following each measurement, the truth measurement of rotation and acceleration obtained by the pair of atomic sensors is compared to the output of the appropriate MEMS sensor set, and a calibration correction is made. The next measurement by the atomic sensor pair may be along the same axis, or along a different axis depending on priorities for MEMS sensor correction. If a different sense axis is desired, then laser optics are switched in order to interrogate the atoms along a different axis. In this example, multiplexing results in a reduction of about three in atomic sensor duty cycle, from about 20% (six atomic sensors without multiplexing) to about 6.7% (two atomic sensors with multiplexing). In other implementations, faster cycle times are possible, depending on desired performance.

In another approach, the axis of laser light can be continuously blended to create a an optical gimbal sensor. In principle, the sense axis for the atomic sensor can be rotated continuously to maintain an orientation along, for instance, the principle axis of rotation, or the net acceleration vector, or any other desired orientation.

The optical gimbal function provides the capability of continuously rotating the input axes of the gyroscope to maintain alignment with an arbitrary axis. Atomic sensor sensitivity scales inversely with dynamic range, and this tradeoff can be adjusted in real time. Adjustments to the sense axis orientations can take advantage of this capability by intelligently choosing how to split the rotation among the gyroscope triad sense axis. This can be used, for instance, to align one gyroscope axis of the triad with the principal axis of rotation. This maximizes the signal on that gyroscope, and minimizes the signal on the gyroscopes orthogonal to the axis of rotation. Such a strategy allows the gyroscope with the most signal to have a high dynamic range (at the cost of lower sensitivity), while maintaining a lower dynamic range (with increased sensitivity) on the other axes. In another approach, the sense axes can be arranged such that the rotation signal is "split" evenly among the sense axes, ensuring that no single axis will require an excessive dynamic range (and corresponding decreased sensitivity).

Aside from the approaches based on the sensitivity/dynamic range tradeoff, another technique is simply to maintain the sense axes in a locally level orientation. Prior to the advent of "strapdown" inertial sensors, all inertial measurement units operated in this way. However, moving parts in conventional gimbaled sensor heads are subject to wear, limiting reliability. The optical gimbal sensor, in contrast, has no moving parts, enabling gimbaled operation without sacrificing reliability. Navigation with gimbaled sensors offers a few performance advantages over strapdown navigation. Because the stabilized sensor platforms experience only very small rotations, instead of the complete vehicle body rotations experienced by a strapdown navigator, they are less sensitive to gyroscope scale factor errors. In addition, gimbaled navigation systems may be rotated during ground alignment procedures or in flight (independently of the vehicle) to reduce the effect of sensor bias errors, an option not available with strapdown systems.

The present approach achieves low size, weight, and power by extracting six degrees of inertial freedom from a single pair of atomic inertial sensors. This is accomplished by using an optical multiplexer, which drives the optical switches in selecting specific axes along which to apply laser light when manipulating the atoms in the atomic sensor pair. The switching function determines the orientation of laser light within the sensor package. Changing orientation of the laser light changes the sense axis for the atomic sensor.

FIG. 1 is a block diagram of an inertial sensing system 100, such as for an IMU, which employs multi-axis atomic inertial sensors according to one embodiment. The sensing system 100 includes a pair of multi-axis atomic inertial sensors, including a first atomic inertial sensor 102 and a second atomic inertial sensor 104, as well as a plurality of MEMS inertial sensors, such as at least one MEMS gyroscope 106 and at least one MEMS accelerometer 108.

In one implementation, since acceleration and rotation are entangled in atomic inertial sensors 102 and 104, each sensor can act as both an accelerometer and a gyroscope in detecting acceleration and rotation. The two atomic inertial sensors are required in order to distinguish how much phase shift is due to acceleration and how much is due to rotation. These sensors are operated in reciprocal fashion leading to a sign change for rotation but not for acceleration. This allows the atomic inertial sensors to distinguish how much phase shift is due to acceleration and how much is due to rotation. In an alternative implementation, one of the atomic inertial sensors is sensitive to both acceleration and rotation, and the other sensor is sensitive only to acceleration.

In one embodiment, the atomic inertial sensors and the MEMS inertial sensors operatively communicate with each other through a closed loop feedback unit 110. Further details of a MEMS/atomic closed feedback loop are described in U.S. Provisional Application No. 61/665,061, filed on Jun. 27, 2012, entitled CLOSED LOOP ATOMIC INERTIAL SENSOR, the disclosure of which is incorporated by reference.

The inertial sensing system 100 also includes an optical multiplexer 114 in operative communication with atomic inertial sensors 102 and 104. The optical multiplexer is described in further detail hereafter with respect to FIG. 2.

An output signal from atomic inertial sensor 102 is sent to an atomic inertial sensor compensation unit 118, and an output signal from atomic inertial sensor 104 is sent to an atomic inertial sensor compensation unit 120. The compensation units 118 and 120 provide sensor corrections based on a factory calibration.

An output signal from MEMS gyroscope 106 is sent to a MEMS gyroscope compensation unit 122, and an output signal from MEMS accelerometer 108 is sent to a MEMS accelerometer compensation unit 124. The compensation units 122 and 124 provide for error correction of the MEMS inertial sensors.

A linear or non-linear fusion algorithm or filter 128, such as a particle filter, receives output signals from the atomic inertial sensor compensation units 118, 120 and the MEMS compensation units 122, 124. The fusion algorithm 128 outputs a feedback signal to MEMS compensation units 122 and 124 to provide for error correction. By comparing the MEMS measurement and atomic measurements at a particular time, errors in the MEMS inertial sensor outputs can be estimated and corrected using the fusion algorithm 128.

In addition, the output signal from MEMS gyroscope compensation unit 122 can be optionally sent to a coning module 132 and a sculling module 134 for applying high speed corrections to output signals of MEMS gyroscope 106. In this case, a corrected signal is sent from coning module 132 to an adder 136, which also receives the original signal from compensation unit 122 and outputs a delta theta ($\theta$) signal. In addition, a corrected signal is sent from sculling module 134 to an adder 138, which also receives the original signal from compensation unit 124 and outputs a delta velocity (v) signal.

In addition, the output signal from MEMS accelerometer compensation unit 124 can be optionally sent to sculling module 134 for applying high speed corrections to output signals of MEMS accelerometer 108. In this case, a corrected signal is sent from sculling module 134 to an adder 138, which also receives the original signal from compensation unit 124 and outputs a delta velocity (v) signal.

Figure 2:
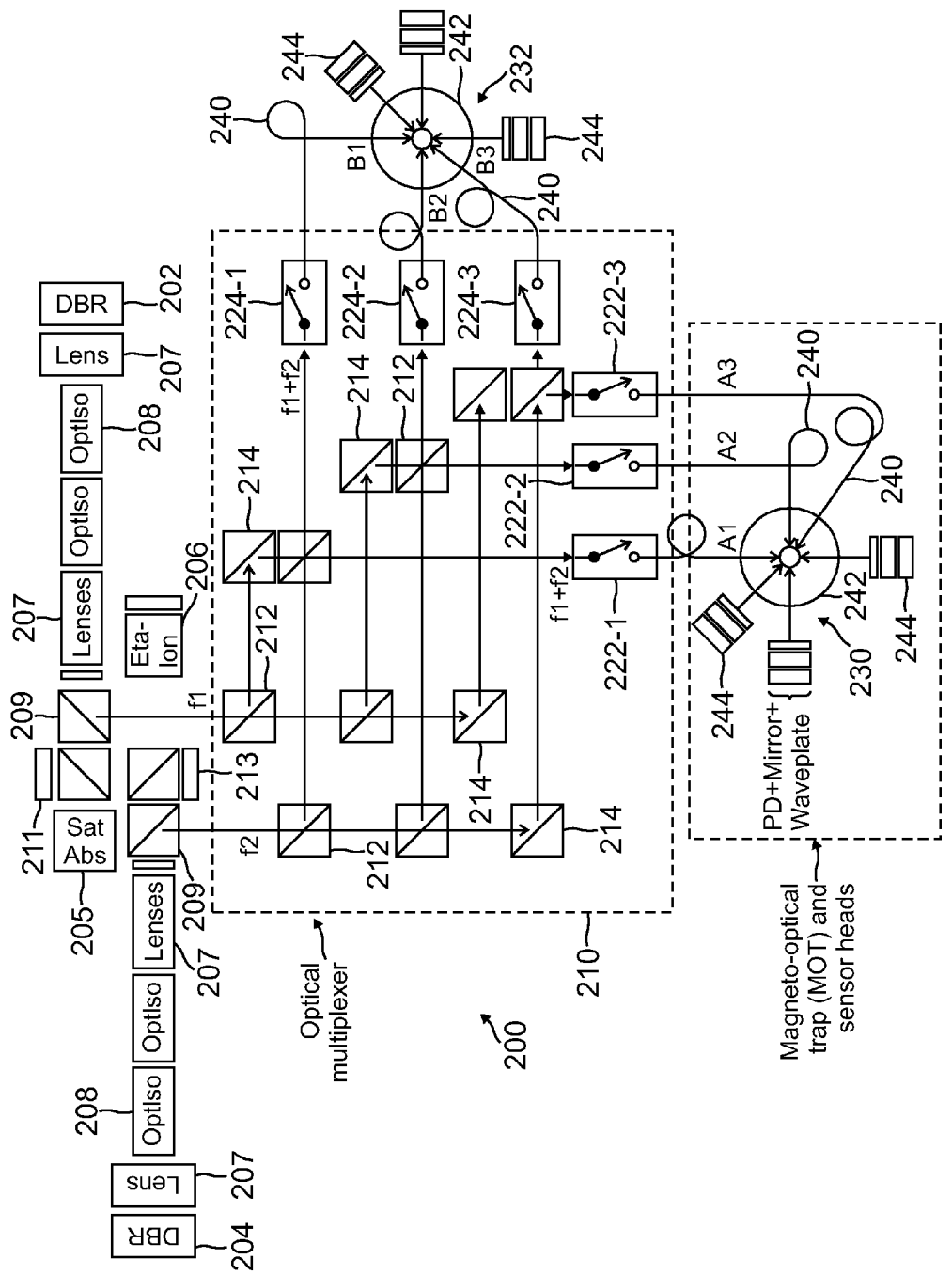
FIG. 2 is a block diagram of a multi-axis atomic inertial sensor apparatus according to one embodiment.

FIG. 2 is a block diagram of a multi-axis atomic inertial sensor apparatus 200 according to one embodiment. The sensor apparatus 200 includes a plurality of laser devices, such as a first laser device 202, which can be a distributed Bragg reflector (DBR), and a second laser device 204, which can also be a DBR. In another embodiment, one or both of the laser devices can be a vertical-cavity surface-emitting laser (VCSEL).

The laser devices 202 and 204 can be frequency locked to a vapor cell of an atomic sensor by saturated absorption spectroscopy 205 or an etalon 206. The laser devices 202 and 204 are in optical communication with an optical multiplexer 210 through various optical components, such as one or more lenses 207, optical isolators 208, beam splitters 209, and the like.

Saturated absorption can be used to lock laser device 202 to an atomic transition. In saturated absorption, the laser light shines through the vapor cell, and is retro-reflected back onto the same beam path. This technique selects only zero velocity atoms for interaction with the light. Doppler broadening of the atomic transition is therefore eliminated, resulting in a very narrow absorption line that is detected by a photodetector 211. The narrow absorption line allows for precise and stable locking of the laser frequency.

For bichromatic transitions, it is desirable to phase lock laser devices 202 and 204 so that they provide a coherent electromagnetic field to the atoms in the vapor cell. One technique for phase locking laser devices 202 and 204 is to shine both of their laser beams onto a common photodetector 213, where the beams interfere with one another. The laser devices 202 and 204 can differ in frequency by a few GHz. The frequency difference modulates the laser interference at a few GHz, resulting in a radio-frequency (RF) output signal from photodetector 213 of a few GHz. This RF signal is then compared to a stable RF reference signal. Differences between the photodetector signal and the reference signal result in an error signal that is fed back to correct phase or frequency of one of the laser devices, so that the relative frequency and phase of the two laser devices is stabilized. In this example, one laser device is the master and the other laser device is the slave. In another example, two slave lasers can be locked to a single master laser, which affords greater flexibility in the range over which both slave lasers can be locked.

The multiplexer 210 includes a plurality of optical components, such as a plurality of beam splitters 212 and reflectors 214, which are configured to direct a light beam having a first frequency (f1) from laser device 202 and a light beam having a second frequency (f2) from laser device 204 to various optical switches that are coupled to a pair of atomic inertial sensors 230 and 232. In one example, the Raman frequency (f1-f2) is about a few GHz, corresponding to the hyperfine splitting of an alkali atom, such as rubidium (6.8 GHz) or cesium (9.2 GHz). In another example, the Bragg/Bloch frequency (f1-f2) is about 10 kHz and can be ramped to induce absorption of multiple quanta of photon momenta, to enhance sensor scale factor.

In an exemplary embodiment, a first set of optical switches 222-1, 222-2, and 222-3 in multiplexer 210 are configured to sequentially direct the light beams along different orientation axes A-1, A-2, and A-3 (e.g., x, y, z axes) to atomic sensor 230. A second set of optical switches 224-1, 224-2, and 224-3 are configured to sequentially direct laser light along different orientation axes B-1, B-2, and B-3 (e.g., x, y, z axes) to atomic sensor 232.

In one embodiment, an optical fiber 240 can be coupled to the output of each of the optical switches to direct laser light to respective inputs of atomic sensors 230 and 232. The optical switches switch on different axes or combinations of axes to make the atomic sensors sensitive to acceleration or rotation along different axes.

The atomic sensors 230 and 232 sequentially measure motion with respect to all three coordinate axes by selecting light beam pairs that are oriented orthogonal (rotation) and parallel (acceleration) to those axes. In one embodiment, atomic sensors 230 and 232 each comprise a magneto-optical trap (MOT) 242, and sensor heads 244 that include a photodetector (PD), a mirror, and a waveplate, which are aligned with the beams input into the atomic sensors. During MOT operation, all switches are on, so that laser cooling occurs along all axes. Following laser cooling, some of the switches are shut off in order to perform interferometry along selected axes.

Figures 3A, 3B:
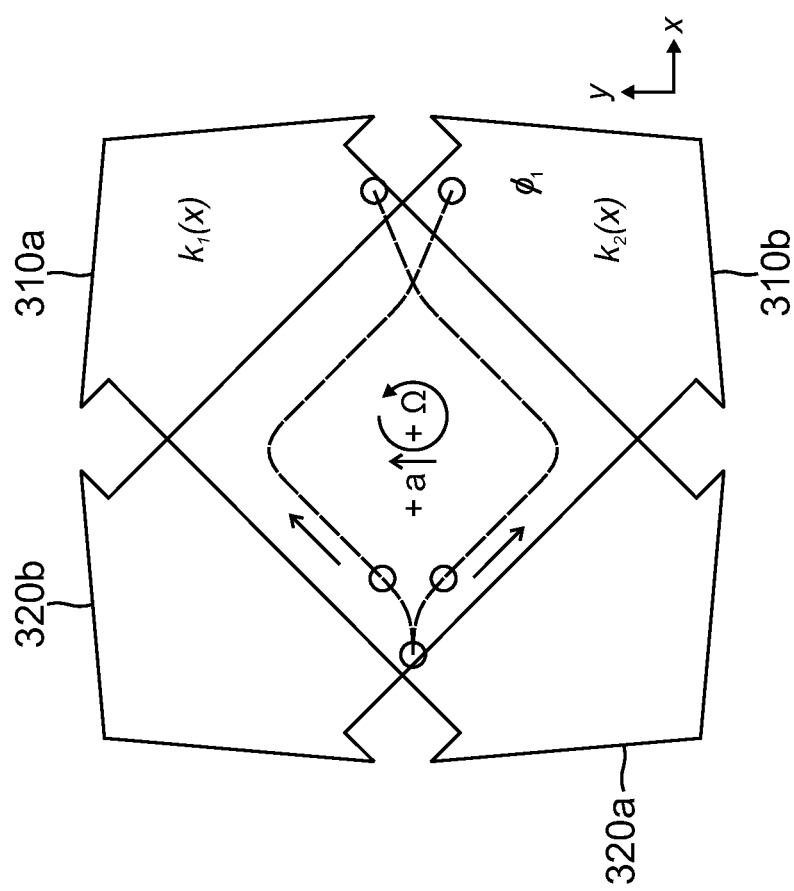
FIG. 3A is a schematic diagram showing an exemplary interferometer trajectory in a multi-axis atomic inertial sensor according to one embodiment.
FIG. 3B is a table listing the possible combinations of laser orientations, with corresponding axes of sensitivity.

FIG. 3A shows an exemplary interferometer trajectory in a multi-axis atomic inertial sensor according to one embodiment, which utilizes a moving Bragg lattice for feedback. The interferometer in the atomic inertial sensor is created by two pairs of counter-propagating beams 310a, 310b and 320a, 320b, which intersect atoms in the sensor. The wave vectors (k) of the beams determine the trajectory of the atoms, and therefore the axes of sensitivity for acceleration ($\alpha$) and rotation ($\Omega$).

Possible combinations of laser orientations, with corresponding axes of sensitivity are shown in the table of FIG. 3B. In general, the laser light is applied along two wave vectors. The table in FIG. 3B tabulates the three possible pairings of wave vectors, along with the corresponding axes of rotation and acceleration. The first row in the table with $\Omega$=k and $\alpha$=j is equivalent to the example shown in FIG. 3A.

During an interferometry cycle, the pair of beams divides the quantum mechanical wave function of each of the laser cooled atoms, so that there is a 50% probability of finding the atom either above or below the axis of separation. Modulation of laser frequency and amplitude guides each half of the wave function along the trajectory shown in FIG. 3A. Upon recombination of the wave function halves into whole atoms, the quantum mechanical phase of the atom has acquired a phase shift that is proportional to rotation and acceleration. This phase shift can be read out by subsequent imaging of cloud position and/or internal state detection.

EXAMPLE EMBODIMENTS

Example 1 includes an inertial sensing system comprising a first multi-axis atomic inertial sensor, a second multi-axis atomic inertial sensor, and an optical multiplexer optically coupled to the first and second multi-axis atomic inertial sensors. The optical multiplexer is configured to sequentially direct light along different axes of the first and second multi-axis atomic inertial sensors. A plurality of MEMS inertial sensors are in operative communication with the first and second multi-axis atomic inertial sensors. Output signals from the first and second multi-axis atomic inertial sensors aid in correcting errors produced by the MEMS inertial sensors by sequentially updating output signals from the MEMS inertial sensors.

Example 2 includes the system of Example 1, wherein the first multi-axis atomic inertial sensor is configured to detect acceleration and rotation.

Example 3 includes the system of Example 2, wherein the second multi-axis atomic inertial sensor is configured to detect acceleration and rotation.

Example 4 includes the system of Example 2, wherein the second multi-axis atomic inertial sensor is configured to detect only acceleration.

Example 5 includes the system of any of Examples 1-4, wherein the MEMS inertial sensors comprise at least one MEMS gyroscope and at least one MEMS accelerometer.

Example 6 includes the system of any of Examples 1-5, wherein the MEMS inertial sensors operatively communicate with the first and second multi-axis atomic inertial sensors through a closed loop feedback.

Example 7 includes the system of any of Examples 1-6, further comprising a first atomic inertial sensor compensation unit that receives an output signal from the first multi-axis atomic inertial sensor, wherein the first atomic inertial sensor compensation unit provides sensor corrections based on a factory calibration.

Example 8 includes the system of any of Examples 1-7, further comprising a second atomic inertial sensor compensation unit that receives an output signal from the second multi-axis atomic inertial sensor, wherein the second atomic inertial sensor compensation unit provides sensor corrections based on a factory calibration.

Example 9 includes the system of any of Examples 5-8, further comprising a MEMS gyroscope compensation unit that receives an output signal from the MEMS gyroscope, wherein the MEMS gyroscope compensation unit aids in correcting errors produced by the MEMS gyroscope.

Example 10 includes the system of any of Examples 5-9, further comprising a MEMS accelerometer compensation unit that receives an output signal from the MEMS accelerometer, wherein the MEMS accelerometer compensation unit aids in correcting errors produced by the MEMS accelerometer.

Example 11 includes the system of any of Examples 7-10, further comprising a fusion filter that receives output signals from each of the first atomic inertial sensor compensation unit, the second atomic inertial sensor compensation unit, the MEMS gyroscope compensation unit, and the MEMS accelerometer compensation unit, wherein the fusion filter outputs a feedback signal to the MEMS gyroscope compensation unit and the MEMS accelerometer compensation unit to aid in error correction of the MEMS gyroscope and the MEMS accelerometer.

Example 12 includes the system of any of Examples 1-11, wherein the system is part of an inertial measurement unit.

Example 13 includes a multi-axis atomic inertial sensor apparatus comprising a first laser device that outputs a light beam having a first frequency, a second laser device that outputs a light beam having a second frequency, and an optical multiplexer in optical communication with the first and second laser devices, the optical multiplexer including a plurality of optical switches. A first multi-axis atomic inertial sensor is in optical communication with the optical multiplexer, and a second multi-axis atomic inertial sensor is in optical communication with the optical multiplexer. The optical multiplexer is configured to sequentially direct the light beams from the first and second laser devices along different axes of the first and second multi-axis atomic inertial sensors.

Example 14 includes the apparatus of Example 13, wherein the first multi-axis atomic inertial sensor is configured to detect acceleration and rotation.

Example 15 includes the apparatus of Example 14, wherein the second multi-axis atomic inertial sensor is configured to detect acceleration and rotation.

Example 16 includes the apparatus of Examples 14, wherein the second multi-axis atomic inertial sensor is configured to detect only acceleration.

Example 17 includes the apparatus of any of Examples 13-16, wherein the optical switches comprise a first set of three optical switches configured to sequentially direct the light beams along three different orientation axes of the first multi-axis atomic inertial sensor, and a second set of three optical switches configured to sequentially direct the light beams along three different orientation axes of the second multi-axis atomic inertial sensor.

Example 18 includes the apparatus of any of Examples 13-17, further comprising a plurality of MEMS inertial sensors in operative communication with the first and second multi-axis atomic inertial sensors, wherein the MEMS inertial sensors comprise at least one MEMS gyroscope and at least one MEMS accelerometer.

Example 19 includes the apparatus of Example 18, wherein the apparatus is configured as an optical gimbal sensor.

Example 20 includes a method for inertial sensing, wherein the method comprises providing a first multi-axis atomic inertial sensor and a second multi-axis atomic inertial sensor; transmitting a pair of laser beams through an optical multiplexer that sequentially directs the laser beams along different axes of the first and second multi-axis atomic inertial sensors; and outputting signals from the first and second multi-axis atomic inertial sensors to aid in correcting errors produced by one or more MEMS inertial sensors by sequentially updating output signals from the MEMS inertial sensors.

Although specific embodiments have been illustrated and described herein, it will be appreciated by those of ordinary skill in the art that any arrangement, which is calculated to achieve the same purpose, may be substituted for the specific embodiments shown. Therefore, it is manifestly intended that this invention be limited only by the claims and the equivalents thereof.

What is claimed is:

1. An inertial sensing system, comprising:
   a first multi-axis atomic inertial sensor;
   a second multi-axis atomic inertial sensor;
   an optical multiplexer optically coupled to the first and second multi-axis atomic inertial sensors, the optical multiplexer configured to sequentially direct light along different axes of the first and second multi-axis atomic inertial sensors; and
   a plurality of micro-electrical-mechanical systems (MEMS) inertial sensors in operative communication with the first and second multi-axis atomic inertial sensors;
   wherein output signals from the first and second multi-axis atomic inertial sensors aid in correcting errors produced by the MEMS inertial sensors by sequentially updating output signals from the MEMS inertial sensors.

2. The system of claim 1, wherein the first multi-axis atomic inertial sensor is configured to detect acceleration and rotation.

3. The system of claim 2, wherein the second multi-axis atomic inertial sensor is configured to detect acceleration and rotation.

4. The system of claim 2, wherein the second multi-axis atomic inertial sensor is configured to detect only acceleration.

5. The system of claim 1, wherein the MEMS inertial sensors comprise at least one MEMS gyroscope and at least one MEMS accelerometer.

6. The system of claim 5, further comprising a first atomic inertial sensor compensation unit that receives an output signal from the first multi-axis atomic inertial sensor, wherein the first atomic inertial sensor compensation unit provides sensor corrections based on a factory calibration.

7. The system of claim 6, further comprising a second atomic inertial sensor compensation unit that receives an output signal from the second multi-axis atomic inertial sensor, wherein the second atomic inertial sensor compensation unit provides sensor corrections based on a factory calibration.

8. The system of claim 7, further comprising a MEMS gyroscope compensation unit that receives an output signal from the MEMS gyroscope, wherein the MEMS gyroscope compensation unit aids in correcting errors produced by the MEMS gyroscope.

9. The system of claim 8, further comprising an MEMS accelerometer compensation unit that receives an output signal from the MEMS accelerometer, wherein the MEMS accelerometer compensation unit aids in correcting errors produced by the MEMS accelerometer.

10. The system of claim 9, further comprising a fusion filter that receives output signals from each of the first atomic inertial sensor compensation unit, the second atomic inertial sensor compensation unit, the MEMS gyroscope compensation unit, and the MEMS accelerometer compensation unit, wherein the fusion filter outputs a feedback signal to the MEMS gyroscope compensation unit and the MEMS accelerometer compensation unit to aid in error correction of the MEMS gyroscope and the MEMS accelerometer.

11. The system of claim 1, wherein the MEMS inertial sensors operatively communicate with the first and second multi-axis atomic inertial sensors through a closed loop feedback.

12. The system of claim 1, wherein the system is part of an inertial measurement unit.

13. A multi-axis atomic inertial sensor apparatus, comprising:
   a first laser device that outputs a light beam having a first frequency;
   a second laser device that outputs a light beam having a second frequency;
   an optical multiplexer in optical communication with the first and second laser devices, the optical multiplexer including a plurality of optical switches;
   a first multi-axis atomic inertial sensor in optical communication with the optical multiplexer;
   a second multi-axis atomic inertial sensor in optical communication with the optical multiplexer;
   wherein the optical multiplexer is configured to sequentially direct the light beams from the first and second laser devices along different axes of the first and second multi-axis atomic inertial sensors.

14. The apparatus of claim 13, wherein the first multi-axis atomic inertial sensor is configured to detect acceleration and rotation.

15. The apparatus of claim 14, wherein the second multi-axis atomic inertial sensor is configured to detect acceleration and rotation.

16. The apparatus of claim 14, wherein the second multi-axis atomic inertial sensor is configured to detect only acceleration.

17. The apparatus of claim 13, wherein the optical switches comprise:
   a first set of three optical switches configured to sequentially direct the light beams along three different orientation axes of the first multi-axis atomic inertial sensor; and
   a second set of three optical switches configured to sequentially direct the light beams along three different orientation axes of the second multi-axis atomic inertial sensor.

18. The apparatus of claim 13, further comprising a plurality of micro-electrical-mechanical system (MEMS) inertial sensors in operative communication with the first and second multi-axis atomic inertial sensors, wherein the MEMS inertial sensors comprise at least one MEMS gyroscope and at least one MEMS accelerometer.

19. The apparatus of claim 18, wherein the apparatus is configured as an optical gimbal sensor.

20. A method for inertial sensing, the method comprising:
   providing a first multi-axis atomic inertial sensor and a second multi-axis atomic inertial sensor;
   transmitting a pair of laser beams through an optical multiplexer that sequentially directs the laser beams along different axes of the first and second multi-axis atomic inertial sensors; and
   outputting signals from the first and second multi-axis atomic inertial sensors to aid in correcting errors produced by one or more micro-electrical-mechanical systems (MEMS) inertial sensors by sequentially updating output signals from the MEMS inertial sensors.

* * * * *